United States Patent
Hosaka et al.

(10) Patent No.: US 8,912,371 B2
(45) Date of Patent: Dec. 16, 2014

(54) METHOD OF PRODUCING A CHLORINATED HYDROCARBON HAVING 3 CARBON ATOMS

(75) Inventors: Shunsuke Hosaka, Shunan (JP); Yasutaka Komatsu, Shunan (JP); Masayuki Moriwaki, Shunan (JP); Kikuo Yamamoto, Shunan (JP); Naoya Okada, Shunan (JP)

(73) Assignee: Tokuyama Corporation, Shunan-Shi (JP)

( * ) Notice: Subject to any disclaimer, the term of this patent is extended or adjusted under 35 U.S.C. 154(b) by 0 days.

(21) Appl. No.: 13/819,998

(22) PCT Filed: Dec. 1, 2011

(86) PCT No.: PCT/JP2011/078361
§ 371 (c)(1),
(2), (4) Date: Feb. 28, 2013

(87) PCT Pub. No.: WO2012/081482
PCT Pub. Date: Jun. 21, 2012

(65) Prior Publication Data
US 2013/0165705 A1 Jun. 27, 2013

(30) Foreign Application Priority Data

Dec. 16, 2010 (JP) ................................ 2010-280084
May 11, 2011 (JP) ................................ 2011-106055
Jun. 7, 2011 (JP) ................................ 2011-127409
Jun. 8, 2011 (JP) ................................ 2011-128380

(51) Int. Cl.
C07C 17/10 (2006.01)
C07C 17/25 (2006.01)
C07C 17/06 (2006.01)
C07C 19/01 (2006.01)
C07C 21/04 (2006.01)

(52) U.S. Cl.
CPC ................. *C07C 17/06* (2013.01); *C07C 17/10* (2013.01); *C07C 17/25* (2013.01)

USPC ........... 570/227; 570/254; 570/252; 570/253; 570/231

(58) Field of Classification Search
CPC ..................................................... C07C 17/013
USPC .......... 570/101, 144, 252, 253, 254, 227, 231
See application file for complete search history.

(56) References Cited

U.S. PATENT DOCUMENTS 3,732,322 A 5/1973 Kawaguchi et al.
4,535,194 A 8/1985 Woodard
(Continued)

FOREIGN PATENT DOCUMENTS

JP 49-66613 A 6/1974
JP 60-36429 A 2/1985
(Continued)

OTHER PUBLICATIONS

International Preliminary Examination Report dated Jun. 27, 2013 in PCT/JP2011/078361 (Forms PCT/iSA/237; PCT/IB/373 and PCT/IB/338).

(Continued)

*Primary Examiner* — Jafar Parsa
*Assistant Examiner* — Medhanit Bahta
(74) *Attorney, Agent, or Firm* — Birch, Stewart, Kolasch & Birch, LLP

(57) ABSTRACT

A method of producing a chlorinated hydrocarbon having 3 carbon atoms, comprising a conversion step for converting a chloropropane represented by the following formula (1) into a chloropropane represented by the following formula (2) by reacting it with chlorine in the presence of anhydrous aluminum chloride.

$$CCl_3-CCl_{(2-m)}H_m-CCl_{(3-n)}H_n \quad (1)$$

(In the above formula (1), m is 1 or 2, and n is an integer of 0 to 3.)

$$CCl_3-CCl_{(3-m)}H_{(m-1)}-CCl_{(3-n)}H_n \quad (2)$$

(In the above formula (2), m and n are the same integers as in the formula (1), respectively.)

21 Claims, 1 Drawing Sheet

(56) References Cited

U.S. PATENT DOCUMENTS

| | | |
|---|---|---|
| 4,650,914 A | 3/1987 | Woodard |
| 5,659,093 A | 8/1997 | Takubo et al. |
| 7,094,936 B1 * | 8/2006 | Owens et al. .............. 570/257 |
| 8,115,038 B2 | 2/2012 | Wilson et al. |
| 8,304,589 B2 | 11/2012 | Fukuju et al. |
| 2009/0216055 A1 * | 8/2009 | Wilson et al. .............. 570/219 |
| 2009/0240090 A1 | 9/2009 | Merkel et al. |
| 2012/0035402 A1 | 2/2012 | Wilson et al. |
| 2012/0053374 A1 | 3/2012 | Fukuju et al. |
| 2012/0157723 A1 | 6/2012 | Fukuju et al. |
| 2013/0012743 A1 | 1/2013 | Wilson et al. |

FOREIGN PATENT DOCUMENTS

| | | |
|---|---|---|
| JP | 2010-229047 A | 10/2010 |
| JP | 2010-229092 A | 10/2010 |
| JP | 2010-248104 A | 11/2010 |
| WO | WO 2009/085862 A1 | 7/2009 |
| WO | WO 2010/150835 A1 | 12/2010 |

OTHER PUBLICATIONS

International Search Report issued in PCT/JP2011/078361, mailed on Mar. 13, 2012.

* cited by examiner

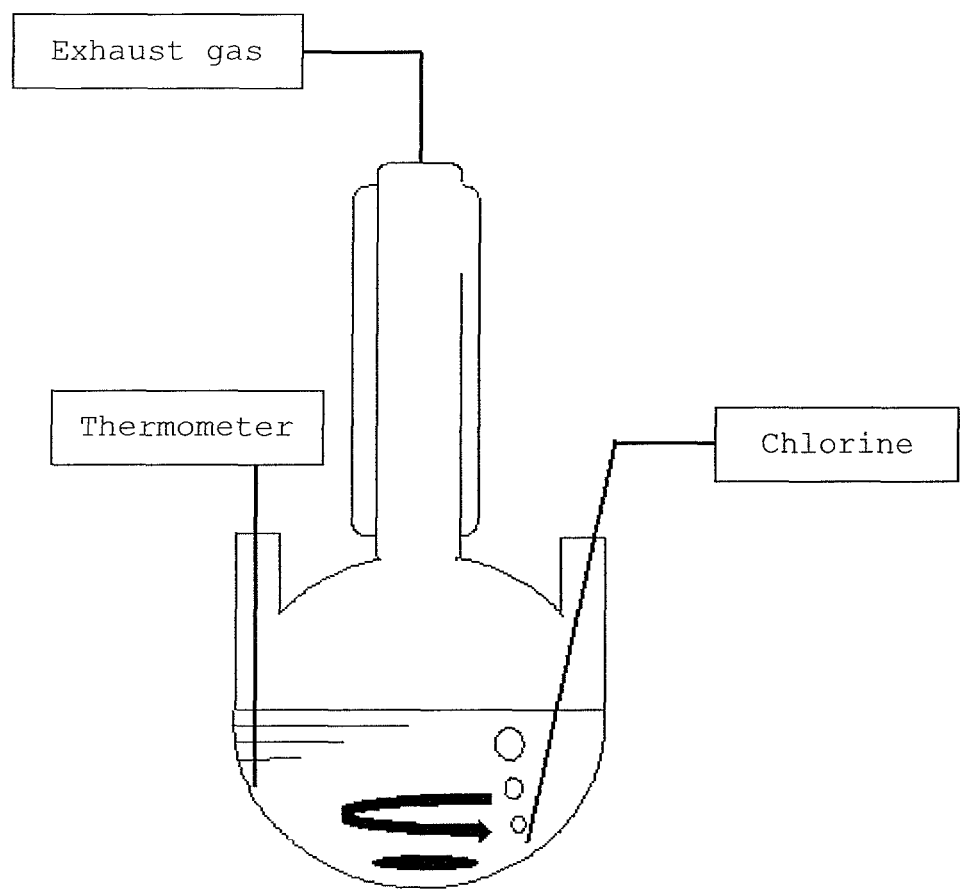

METHOD OF PRODUCING A CHLORINATED HYDROCARBON HAVING 3 CARBON ATOMS

TECHNICAL FIELD

The present invention relates to a method of producing a chlorinated hydrocarbon having 3 carbon atoms. More specifically, it relates to a method of converting a chlorinated hydrocarbon having 3 carbon atoms into a chlorinated hydrocarbon having 3 carbon atoms and one more chlorine atom (polychloropropane) than the above chlorinated hydrocarbon by a single batch process.

Further, the present invention also relates to a method of dehydrochlorinating the product of the above conversion step to convert it into a chlorinated hydrocarbon having 3 carbon atoms (chloropropene or polychloropropene) by controlling the temperature of a reaction system after the above single batch process.

BACKGROUND ART

Polychloropropane is important as a raw material or an intermediate for producing various products such as agricultural chemicals, medicinal products and freon substitutes. For example, trichloroallyl diisopropylthiocarbamate which is useful as a herbicide can be produced from 1,1,1,2,3-pentachloropropane as a starting material through 1,1,2,3-tetrachloropropene.

As a method of producing this polychloropropane, there is known a three-stage reaction consisting of a first reaction for obtaining chloropropane by adding carbon tetrachloride to an unsaturated compound having 2 carbon atoms (nonsubstituted or chlorine-substituted ethylene), a second reaction for obtaining chloropropene by dehydrochlorinating the chloropropane and a third reaction for obtaining chloropropane of interest by further adding chlorine to the chloropropene. As the second reaction and the third reaction particularly relevant to the present invention out of these reactions, for example, U.S. Pat. No. 4,650,914 (document 1) discloses an example in which 1,1,1,2,3-pentachloropropane is obtained by causing an alkaline aqueous solution to act on 1,1,1,3-tetrachloropropane to carry out a dehydrochlorination reaction so as to obtain a mixture of 1,1,3-trichloropropene and 3,3,3-trichloropropene, separating a water phase from the mixture and chlorinating the obtained product by using chlorine.

As for the dehydrochlorination reaction as the second reaction, JP-A 49-66613 (document 2) discloses a method in which the reaction is carried out at a high temperature in the presence of iron chloride as a catalyst.

Further, as a method in which the above second reaction and the above third reaction are carried out in a single step, US Patent Publication 2009/216055 (document 3) discloses a method of obtaining 1,1,1,2,3-pentachloropropane at a stretch by blowing a chlorine gas into 1,1,1,3-tetrachloropropane at a high temperature in the presence of iron chloride as a catalyst.

When the polychloropropane is to be produced by the methods of the above patent documents 1 and 2, the reactions of the two steps must be carried out under completely different conditions, whereby a plurality of reactors are required and the reactions take long, which is uneconomical. When the polychloropropane is to be produced by the method of the patent document 3, the above problems are eliminated due to a single-step reaction. However, a high-temperature reaction is required and the selectivity of a product of interest is unsatisfactory, whereby there is large room for improvement.

Meanwhile, highly chlorinated polychloropropene such as 1,1,2,3-tetrachloropropene is important as a raw material or an intermediate for producing various products such as medicinal and agricultural products and freon substitutes (for example, the above document 3, U.S. Pat. No. 5,659,093 and US Patent Publication 2009/240090).

As one of the methods of producing this polychloropropene, there is known a method in which high-order chlorinated propane having at least one hydrogen atom is dehydrochlorinated to produce a double bond. As for this dehydrochlorination, there are known a method in which high-order chlorinated propane is brought into contact with an alkaline aqueous solution such as a sodium hydroxide aqueous solution in the presence of a phase transfer catalyst (for example, JP-A 2010-229047 and JP-A 2010-229092) and a method in which high-order chlorinated propane is heated in the presence of ferric chloride (for example, the above document 3 and U.S. Pat. No. 3,732,322).

However, when polychloropropene is produced by bringing high-order chlorinated propane into contact with an alkaline aqueous solution, a large amount of alkaline liquid waste which is produced after the reaction must be disposed of. When ferric chloride is used, liquid waste to be disposed of is not substantially produced but there is large room for improvement in terms of reaction conversion and the selectivity of a product of interest.

DISCLOSURE OF THE INVENTION

The present invention was made in view of the above situation and an object of the present invention is as follows.

Firstly, there is provided a method capable of obtaining polychloropropane of interest at a high selectivity without the need for a high-temperature reaction by carrying out the above second reaction and the third reaction in a single step.

Secondly, there is provided a method which does not substantially produce liquid waste to be disposed of when polychloropropene is produced by the dehydrochlorination reaction of the polychloropropane obtained above and is excellent in reaction conversion and the selectivity of a product of interest.

The inventors of the present invention conducted intensive studies to attain the above objects. As a result, they found that the above first and second objects are attained at the same time by using anhydrous aluminum chloride as a catalyst. The present invention was accomplished based on this finding.

The present invention provides a method of producing a chlorinated hydrocarbon having 3 carbon atoms (chloropropane), comprising a conversion step (first converting step) for converting a chloropropane represented by the following formula (1) into a chloropropane represented by the following formula (2) by reacting it with chlorine in the presence of anhydrous aluminum chloride.

$$CCl_3-CCl_{(2-m)}H_m-CCl_{(3-n)}H_n \quad (1)$$

(In the above formula (1) m is 1 or 2, and n is an integer of 0 to 3.)

$$CCl_3-CCl_{(3-m)}H_{(m-1)}-CCl_{(3-n)}H_n \quad (2)$$

(In the above formula (2), m and n are the same integers as in the formula (1), respectively.)

Further, the present invention also provides a method of producing a chlorinated hydrocarbon having 3 carbon atoms (chloropropene), wherein m in the above formula (1) is 2, and the method further comprises a second conversion step for converting the chloropropane represented by the above formula (2) into a chloropropane represented by the following formula (3) by raising the temperature of a reaction system by 30° C. or more after the supply of chlorine into a reactor is stopped after the above conversion step.

$$CCl_2=CCl—CCl_{(3-n)}H_n \quad (3)$$

(In the above formula (3), n is the same integer as in the formula (1).)

BRIEF DESCRIPTION OF THE DRAWINGS

FIG. 1 is a diagram for explaining the structure of a reactor used in Examples.

BEST MODE FOR CARRYING OUT THE INVENTION

The present invention will be described in detail hereinunder.

The compound used as a raw material in the present invention is a chloropropane represented by the formula (1). Specific examples of the chloropropane represented by the formula (1) include 1,1,1-trichloropropane, 1,1,1,3-tetrachloropropane, 1,1,1,2-tetrachloropropane, 1,1,1,2,3-pentachloropropane, 1,1,1,3,3-pentachloropropane and 1,1,1,2,3,3-hexachloropropane.

The method of obtaining the chloropropane represented by the formula (1) is not particularly limited. When n in the formula (1) is an integer of 0 to 2, the chloropropane is generally obtained by adding carbon tetrachloride to an unsaturated hydrocarbon having 2 carbon atoms represented by the following formula (0).

$$CCl_{(2-m)}H_m=CCl_{(2-n)}H_n \quad (0)$$

(In the above formula (0), m and n are the same integers as in the formula (1), respectively, but n cannot be 3.) Examples of the unsaturated hydrocarbon having 2 carbon atoms represented by the formula (0) include ethylene, vinyl chloride, 1,1-dichloroethylene, 1,2-dichloroethylene and 1,1,2-trichloroethylene.

This addition reaction is generally carried out in the presence of a suitable catalyst. Examples of the catalyst used include iron-phosphate catalysts, iron-aprotic polar solvent catalysts and copper-amine catalysts. Out of these, iron-phosphate catalysts are preferably used. When the above addition reaction is carried out in the presence of an iron-phosphate catalyst, a product in which the carbon of carbon tetrachloride is bonded to a carbon atom on a side with a relatively small number of chlorine atoms is obtained. Therefore, when ethylene is used as a raw material compound, 1,1,1,3-tetrachloropropane is obtained and when vinyl chloride is used, 1,1,1,3,3-pentachloropropane is obtained.

A detailed description is subsequently given of an example in which the typical addition reaction of carbon tetrachloride to an unsaturated hydrocarbon having 2 carbon atoms represented by the formula (0) is carried out by using an iron-phosphate catalyst.

Carbon tetrachloride, iron and a phosphate are put into a reactor whose temperature and pressure have been controlled to ensure that carbon tetrachloride is existent as a liquid phase, and the unsaturated compound having 2 carbon atoms represented by the formula (0) is continuously supplied into the reactor preferably as a gas. The supply of the unsaturated compound having 2 carbon atoms may be started before or after iron and the phosphate are put into the reactor. At this point, it is preferred that all the predetermined amount of iron should be put into the reactor from the beginning. All the predetermined amount of the phosphate may be put into the reactor from the beginning, or only part of the predetermined amount of the phosphate may be put into the reactor at the beginning and the rest of the phosphate may be added while the progress of the addition reaction is monitored. The progress of the addition reaction (reaction rate) can be known from the consumption rate of the unsaturated compound having 2 carbon atoms.

Examples of the iron used herein include metal iron, pure iron, soft iron, carbon steel, ferrosilicon steel and alloys containing iron (such as stainless steel). The iron may have an arbitrary shape such as a powdery, particulate, massive, rod-like, spherical, plate-like or fibrous shape, or may be a metal piece or distillation infill obtained by processing it.

Examples of the phosphate include trimethyl phosphate, triethyl phosphate, tripropyl phosphate, tributyl phosphate, diethyl phosphate, dibutyl phosphate, monophenyl phosphate, monobutyl phosphate, dimethylphenyl phosphate, diethylphenyl phosphate, dimethyethyl phosphate and phenyl ethyl methyl phosphate. Out of these, trialkyl phosphates are preferred, and trialkyl phosphates whose alkyl groups have 1 to 4 carbon atoms are particularly preferred.

The reaction temperature of the addition reaction is preferably 90 to 160° C., more preferably 105 to 130° C. During the reaction, the ethylene pressure in a gas phase part is preferably kept at 0.11 to 0.52 MPa (abs) as a value at 25° C.

The reaction mixture obtained by the above method comprises the chloropropane represented by the formula (1) as the main component, carbon tetrachloride and the unsaturated compound having 2 carbon atoms as unreacted raw materials; and iron, a phosphate and ferric chloride derived from the catalyst as impurities. To use this reaction mixture as a raw material in the step of converting the chloropropane represented by the formula (1) into the chloropropane represented by the formula (2), all the above impurities do not need to be removed but only the phosphate must be removed. The phosphate must be removed because it serves as a catalyst which inhibits the dehydrochlorination reaction. Although the other impurities do not inhibit the reaction, they may be removed. In the step of removing impurities from the above reaction mixture, distillation, column separation or adsorption may be employed.

When the phosphate is removed by distillation, collection operation should be performed in consideration of the relationship between the boiling points of the chloropropane represented by the formula (1) and the boiling point of the phosphate in use.

For example, when the boiling point of the phosphate is higher than the boiling point of the chloropropane represented by the formula (1), the phosphate can be removed by simple distillation for collecting materials having a lower boiling point than the boiling point of the phosphate. For example, when the chloropropane represented by the formula (1) is 1,1,1,3-tetrachloropropane, examples of the phosphate having a higher boiling point than the boiling point of the chloropropane include trimethyl phosphate, triethyl phosphate, triisopropyl phosphate, tributyl phosphate and triphenyl phosphate. Most of the phosphates have a higher boiling point than the boiling point of the chloropropane represented by the formula (1) obtained by the above production method.

In the operation of purifying the reaction mixture to be supplied to the first conversion step, only the phosphate must be removed as described above. When the chloropropane represented by the formula (1) is collected as a low-boiling fraction, other materials having a lower boiling point than the boiling point of the phosphate (such as unreacted raw materials and a chlorinated hydrocarbon as a by-product) are collected together with the chloropropane. The collected low-boiling fraction may be supplied to the first conversion step without problems while it contains these other materials. That is, the feature of the first conversion step is that it is not necessary to carry out fractional distillation for collecting the chloropropane represented by the formula (1) and having high purity and that simple distillation such as distillation through a pot still suffices.

A detailed description is subsequently given of the removal of the phosphate by distillation when the unsaturated hydrocarbon having 2 carbon atoms represented by the formula (0) is ethylene and the phosphate is triethyl phosphate. When the unsaturated hydrocarbon having 2 carbon atoms represented by the formula (0) is ethylene, 1,1,1,3-tetrachloropropane is obtained as the chloropropane represented by the formula (1). The boiling point of triethyl phosphate is higher than the boiling point of 1,1,1,3-tetrachloropropane. Therefore, triethyl phosphate having a higher boiling point than the boiling point of 1,1,1,3-tetrachloropropane can be removed by carrying out simple distillation for collecting materials having a lower boiling point than the boiling point of triethyl phosphate. At this point, high-boiling impurities such as iron and ferric chloride are removed at the same time.

The materials having a lower boiling point than the boiling point of triethyl phosphate include 1,1,1,3-tetrachloropropane of interest and also chlorinated hydrocarbons such as unreacted carbon tetrachloride and by-produced chloroform as main impurities. However, these materials do not have an adverse effect on the first conversion step directly. Therefore, all of them can be collected together and supplied to the first conversion step directly.

Even when materials having a lower boiling point than the boiling point of the chloropropane represented by the formula (1) are further separated by distillation, there occurs no problem except that an apparatus, time and cost for fractional distillation are additionally required.

Any distillation tower known in the industry may be used for distillation. A staged tower or a packed tower is preferred as the distillation tower. Distillation is aimed to remove only the phosphate. Since there is a big difference between the boiling point of triethyl phosphate and the boiling point of 1,1,1,3-tetrachloropropane, triethyl phosphate can be removed in a small number of stages. The upper limit of the number of stages of the staged tower or the number of corresponding stages of the distillation tower in terms of a staged tower is not particularly limited. However, when the number of stages or the number of corresponding stages is too large, the cost of distillation equipment rises. Therefore, the number of stages is preferably 1 to 20, more preferably 1 to 5.

A cross tray or a shower tray may be used in the above staged tower. When a packed distillation apparatus is used, a known infill such as a Raschig ring or a Lessing ring may be used and its material is not limited and may be a metal.

Distillation conditions are not particularly limited. For example, distillation can be carried out by setting the distillation pressure to normal pressure (101 kPa) and the temperature of the top of the distillation tower to a temperature close to the boiling point of the chloropropane represented by the formula (1). However, since the temperature of the bottom of the tower becomes high when the temperature of the top of the distillation tower is made too high, the decomposition of the chloropropane represented by the formula (1) is promoted. When the temperature of the top of the distillation tower is made too low, energy for cooling the top of the distillation tower grows at the time of distillation and the distillation pressure must be made very low, thereby boosting the equipment cost and the operation cost. In consideration of these, the temperature of the bottom of the tower at the time of distillation is in the range of preferably 20 to 200° C., more preferably 50 to 150° C., much more preferably 70 to 120° C. The pressure at the time of distillation may be set to a value which ensures that the chloropropane represented by the formula (1) vaporizes at the above temperature and the vapor reaches the top of the distillation tower. This suitable pressure which differs according to the type of the chloropropane represented by the formula (1) and the temperature of the top of the distillation tower may be set to, for example, 1 to 110 kPa. When the chloropropane represented by the formula (1) is 1,1,1,3-tetrachloropropane, distillation can be carried out at a temperature of the top of the distillation tower at 10 kPa of about 87° C. because the decomposition of 1,1,1,3-tetrachloropropane hardly occurs at this temperature. The above pressure is absolute pressure.

At the time of distillation, an additive may not be added to the reaction mixture. However, to suppress the decomposition of the chloropropane represented by the formula (1), a stabilizer may be added. The stabilizer used herein is, for example, a phenol compound. Examples of the phenol compound include phenols substituted by an alkoxy group and phenols substituted by an allyl group. Out of these, phenols substituted by an allyl group are preferably used. Examples of the phenols substituted by an allyl group include o-allylphenol, m-allylphenol, p-allylphenol, 4-allyl-2-methoxyphenol (eugenol) and 2-methoxy-4-(1-propenyl)phenol (isoeugenol). These allyl-substituted phenols may be used alone or in combination.

The phosphate and the materials having a higher boiling point than the boiling point of the chloropropane represented by the formula (1) can be removed by carrying out distillation under the above conditions.

The purity of the chloropropane represented by the formula (1) obtained by distillation is not particularly limited but preferably 50 to 100%, more preferably 80 to 99%, much more preferably 90 to 98%. The reason why the upper limits of purity within the more preferred range and the much more preferred range are lower than the upper limit of purity within the preferred range is that it is more preferred to cut the additional purification cost as the first conversion step easily proceeds without setting the purity of the chloropropane represented by the formula (1) to 100%.

Distillation may be carried out in a single tower or several towers.

The amount of the phosphate contained in the chloropropane represented by the formula (1) obtained by this distillation is preferably 10,000 ppmw or less, more preferably 1,000 ppmw or less, much more preferably 100 ppmw or less.

When the phosphate is removed by column separation, if the phosphate is separated from the chloropropane represented by the formula (1), the reaction mixture can be supplied to the first conversion step while it contains a fraction flowing out before or after the chloropropane.

When the phosphate is removed by adsorption, silica gel may be used as an adsorbent. The phosphate is adsorbed to the silica gel by adding the silica gel to the reaction mixture and stirring it and can be removed by removing the silica gel. When the phosphate is removed by adsorption, the reaction mixture can be supplied to the first conversion step while it contains impurities not adsorbed to the adsorbent.

Although the methods of measuring the purity of the chloropropane represented by the formula (1) and the amount of the phosphate are not particularly limited, the purity of the chloropropane and the amount of the phosphate can be determined by gas chromatography using a suitable detector.

A hydrogen flame ionization detector (FID), a thermal conductivity detector or a mass spectrometer may be used as the detector. The concentration of phosphorus of the phosphate can also be determined by means of an inductively-coupled plasma emission spectrometer (ICP-OES).

The method of the present invention can also be applied to 1,1,1-trichloropropane and 1,1,1,2-tetrachloropropane which cannot be produced by adding carbon tetrachloride to the unsaturated hydrocarbon having 2 carbon atoms represented by the formula (0). In this case, a chloropropane produced by a known method may be used as a raw material for these.

In the first conversion step of the method of the present invention, the chloropropane represented by the formula (1) is converted into a chloropropene intermediate in the presence of aluminum chloride and further reacted with chlorine to be converted into the chloropropane represented by the formula (2).

The estimated reaction mechanism of the present invention is as follows.

First, the chloropropane represented by the formula (1) is dehydrochlorinated by the catalytic action of aluminum chloride to produce a chloropropene as an intermediate represented by the following formula.

$$CCl_2\!=\!CCl_{(2-m)}H_{m-1}\!-\!CCl_{(3-n)}H_n$$

(In the above formula, m and n are the same integers as in the formula (1), respectively.)

Thereafter, chlorine is added to the double bond of the above chloropropene intermediate to obtain the chloropropane represented by the formula (2). The chloropropane represented by the formula (2) as a reaction product has another chlorine atom bonded to a carbon atom at the 2-position as compared with the chloropropane represented by the formula (1) as a raw material. Taking an example in which 1,1,1,3-tetrachloropropane is used as the chloropropane represented by the formula (1), 1,1,1,3-tetrachloropropane is first dehydrochlorinated by the catalytic action of aluminum chloride to produce 1,1,3-trichloropropene as an intermediate. Then, it is assumed that chlorine is added to the double bond of this 1,1,3-trichloropropene to produce 1,1,1,2,3-pentachloropropane.

When anhydrous aluminum chloride is not used, a reaction of interest does not proceed selectively. A reaction of interest proceeds selectively by using aluminum chloride, and a compound of interest can be obtained with high selectivity and high yield at a much lower temperature than when a known catalyst (such as iron chloride) is used.

In the method of the present invention, anhydrous aluminum chloride is used. Aluminum chloride hexahydrate does not substantially dissolve in the chloropropane represented by the formula (1). Aluminum hydroxide obtained by reacting aluminum chloride with water does not serve as the catalyst in the method of the present invention. Even when aluminum chloride hexahydrate, aluminum hydroxide or both of them are existent in the reaction system, they do not have an adverse effect on the reaction.

A first preferred mode of the first conversion step of the present invention is carried out by putting at least the chloropropane represented by the formula (1) and anhydrous aluminum chloride into a reactor and then supplying chlorine into the reactor. When anhydrous aluminum chloride in the reactor does not dissolve in the chloropropane represented by the formula (1), a substitution reaction of chlorine for the chloropropane represented by the formula (1) first takes place before the dehydrochlorination of the chloropropane represented by the formula (1) into the chloropropene intermediate. Therefore, when 1,1,1,3-tetrachloropropane is used as the chloropropane represented by the formula (1), a by-product such as 1,1,1,3,3-pentachloropropane is produced and the selectivity of 1,1,1,2,3-pentachloropropane of interest tends to lower. Therefore, the supply of chlorine into the reactor is preferably started after the dissolution of at least part, preferably all of anhydrous aluminum chloride. Whether anhydrous aluminum chloride has dissolved or not can be confirmed from a change in the color of the reaction solution. When anhydrous aluminum chloride has dissolved in, for example, 1,1,1,3-tetrachloropropane (almost achromatic), the reaction solution turns blue.

The amount (concentration) of anhydrous aluminum chloride dissolved is preferably set to a suitable range. When the amount of anhydrous aluminum chloride dissolved in the reaction system is too large, a dimerization reaction between the produced chloropropene intermediates, a dimerization reaction between the chloropropene intermediate and the chloropropane represented by the formula (1) and a dimerization reaction between the chloropropene intermediate and the chloropropane represented by the formula (2) proceed and accordingly, the selectivity of the chloropropane represented by the formula (2) as a compound of interest tends to lower. Therefore, the amount of anhydrous aluminum chloride dissolved is preferably set to a suitable range. It is preferably $2.0 \times 10^{-5}$ to $2.0 \times 10^{-2}$ mol, more preferably $5.0 \times 10^{-5}$ to $1.0 \times 10^{-3}$ mol based on 1 mole of the chloropropane represented by the formula (1) initially injected. The amount of anhydrous aluminum chloride is preferably adjusted to ensure that the concentration thereof falls within the above range when the total amount thereof has dissolved in the chloropropane represented by the formula (1).

The amount of the above anhydrous aluminum chloride dissolved should be understood as the amount substantially existent in the reaction system. As described above, anhydrous aluminum chloride reacts with water to be hydrolyzed into aluminum hydroxide. When water is contained in the chloropropane represented by the formula (1) as a raw material, anhydrous aluminum chloride reacts with this water to produce aluminum hydroxide, thereby reducing the effective amount of the catalyst by this. Therefore, when water is contained in the chloropropane represented by the formula (1), it is preferred to add a large amount of anhydrous aluminum chloride according to the water content so that the substantive amount of anhydrous aluminum chloride dissolved falls within the above range. Therefore, anhydrous aluminum chloride whose amount is ⅓ mol based on 1 mole of water contained in the chloropropane used as a raw material should be added in a larger amount than the desired amount.

The chloropropane represented by the formula (1) may be supplied into the reactor before or after anhydrous aluminum chloride or at the same time as anhydrous aluminum chloride. Predetermined amounts of the chloropropane represented by the formula (1) and anhydrous aluminum chloride may be supplied at a time, or parts of the predetermined amounts thereof may be supplied at the beginning and the rests may be added during the reaction. In either case, a preferred embodiment of the present invention is that the supply of chlorine is started after anhydrous aluminum chloride dissolved in the chloropropane represented by the formula (1) is existent in the reactor.

To ensure that anhydrous aluminum chloride dissolved in the chloropropane represented by the formula (1) is existent in the reactor, for example, anhydrous aluminum chloride and the chloropropane represented by the formula (1) are fed to the reactor and dissolved in the reactor, or a solution prepared by dissolving anhydrous aluminum chloride in a solvent outside the reactor is injected into the reactor and then diluted with the chloropropane represented by the formula (1).

In the former case, only anhydrous aluminum chloride and the chloropropane represented by the formula (1) are substantially existent in a liquid phase in the reactor and chlorine is supplied into this.

The solvent used in the latter case is not particularly limited if it does not inhibit the reaction in the present invention, is easily separated from the product and can dissolve aluminum chloride. More specifically, a solvent which hardly reacts with aluminum chloride, chlorine and a carbon-carbon double bond and has a different boiling point from the boiling point of a product of interest is preferred. Examples of the solvent include chloromethanes such as carbon tetrachloride and chloroform; and ethers such as tetrahydrofuran, dioxane and diethyl ether. However, in consideration of purification operation after the reaction, the chloropropane represented by the formula (1) which is a reaction raw material is preferably used as the solvent. In the case of this preferred mode, only anhydrous aluminum chloride and the chloropropane represented by the formula (1) are substantially existent in the liquid phase in the reactor and chlorine is supplied into this.

To prepare a solution containing anhydrous aluminum chloride dissolved in the solvent outside the reactor, a method in which anhydrous aluminum chloride is mixed with the solvent to be dissolved in the solvent; and a method in which metal aluminum is added to the solvent and at least one chlorinating agent selected from the group consisting of chlorine and hydrogen chloride is supplied into the obtained mixture to chlorinate the metal aluminum into aluminum chloride may be employed. In the case of the latter method, impurities insoluble in the solvent may be produced according to the purity of the metal aluminum. In this case, it is preferred that the aluminum chloride solution after preparation should be supplied into the reactor after the insoluble materials are removed by filtration. To chlorinate the metal aluminum, hydrogen chloride is preferably used. This is because a side reaction may occur when chlorine is used.

To prepare the anhydrous aluminum chloride solution outside the reactor, it is preferred that a solution having a high concentration of anhydrous aluminum chloride should be prepared and diluted with the chloropropane represented by the formula (1) in the reactor to ensure that the concentration of aluminum chloride falls within the above range. The concentration of anhydrous aluminum chloride in this concentrated solution may be, for example, about 1 to 50 g/L.

A second preferred mode of the first conversion step of the present invention is that anhydrous aluminum chloride as a catalyst is obtained by putting the chloropropane represented by the formula (1) and metal aluminum into the reactor and supplying at least one chlorinating agent selected from the group consisting of chlorine and hydrogen chloride into the reactor to chlorinate the metal aluminum into aluminum chloride. Hydrogen chloride is preferably used for chlorination as described above.

Stated more specifically, the chloropropane represented by the formula (1) and metal aluminum are put into the reactor, and a chlorinating agent, preferably hydrogen chloride is supplied into the reactor. In this case, the chlorinating agent is preferably dry. The amount of the metal aluminum should be set to ensure that the concentration of aluminum chloride in the solution obtained after all of this amount is converted into aluminum chloride falls within the above range.

In the case of this mode, most preferably, hydrogen chloride is used as the chlorinating agent for metal aluminum, and chlorine is supplied after hydrogen chloride is supplied until all the amount of the metal aluminum dissolves.

One of the above methods may be used, or two or more of the above methods may be used in combination to prepare the above solution of anhydrous aluminum chloride. However, most preferably, anhydrous aluminum chloride and the chloropropane represented by the formula (1) are fed to the reactor and dissolved in the reactor from the viewpoints of equipment cost, operation time and labor, and the control ease of the purity and concentration of the obtained anhydrous aluminum chloride solution.

Thus, the chloropropane represented by the formula (1) is converted into the chloropropane represented by the formula (2) by supplying chlorine into the reactor in which the chloropropane represented by the formula (1) and anhydrous aluminum chloride preferably dissolved in the chloropropane as a solution are existent. When chlorine is not existent in the reactor, the chloropropane represented by the formula (1) is dehydrochlorinated by the catalytic action of anhydrous aluminum chloride. This dehydrochlorination reaction is promoted more as the temperature of the reaction system becomes higher. The dehydrochlorinated product tends to become a by-product by dimerization or another reaction. Therefore, after anhydrous aluminum chloride and the chloropropane represented by the formula (1) are fed to the reactor, the temperature of the reaction solution is preferably kept low before the supply of chlorine is started. The temperature at which the dehydrochlorination reaction takes place differs according to the number of chlorine atoms of the chloropropane represented by the formula (1). As the number of chlorine atoms increases, a higher temperature is required. Therefore, the temperature before the supply of chlorine and the reaction temperature in the first conversion step will be explained, taking as an example a case where 1,1,1,3-tetrachloropropane is used as the chloropropane represented by the formula (1). When a compound having a larger number of chlorine atoms than that of 1,1,1,3-tetrachloropropane is used as a raw material, the first conversion step can be carried out almost likewise by suitably setting these temperatures higher according to the number of chlorine atoms. The temperatures suitable for the type of the chloropropane can be easily known through a few preliminary experiments conducted by a person having ordinary skill in the art.

When 1,1,1,3-tetrachloropropane is used as the chloropropane represented by the formula (1), the temperature of the reaction solution before the supply of chlorine is kept at preferably 50° C. or lower, more preferably 40° C. or lower. When the temperature of the reaction solution is too low, the dissolution of anhydrous aluminum chloride becomes slow and the concentration of anhydrous aluminum chloride in the chloropropane represented by the formula (1) hardly falls within the above preferred range. Therefore, the temperature of the reaction solution is set to preferably 0° C. or higher, more preferably 10° C. or higher.

As chlorine to be supplied into the reactor may be used ordinary chlorine for industrial use.

In the reactor in the initial stage of the reaction, the concentration of the chloropropane represented by the formula (1) is high and the concentration of the chloropropene intermediate is low. When chlorine is supplied in this state, a chlorine substitution reaction of the chloropropane takes place as a competing reaction besides the dehydrochlorination reaction of the chloropropane. For example, when 1,1,1,3-tetrachloropropane is used as a raw material and the supply of chlorine into the reaction system is large while the concentration of the 1,1,3-trichloropropene intermediate is low in the reaction system and the speed of the dehydrochlorination reaction is slow (for example, the concentration of aluminum chloride is low), the concentration of chlorine in the reaction system becomes too high. As a result, the production of 1,1, 1,3,3-pentachloropropane readily occurs due to a chlorine substitution reaction of 1,1,1,3-tetrachloropropane.

When the concentration of the chloropropene intermediate in the reaction system is too high, side reactions such as a dimerization reaction between the chloropropene intermediates, a dimerization reaction between the chloropropene intermediate and the chloropropane represented by the formula (1) and a dimerization reaction between the chloropropene intermediate and the chloropropane represented by the formula (2) readily occur as described above.

Therefore, the method of the present invention can be carried out with higher selectivity by setting the concentration of anhydrous aluminum chloride dissolved in the chloropropane represented by the formula (1) to the above preferred range and adjusting the timing of starting the supply of chlorine and the chlorine feed rate to suitable values. Stated more specifically, the method is carried out as follows.

The supply of chlorine should be started when the concentration of the chloropropene intermediate produced by the dehydrochlorination reaction becomes preferably 0.1 to 30 mass %, more preferably 0.5 to 20 mass % based on the total mass of the reaction system. The conversion of the chloropropane represented by the formula (1) into the chloropropene intermediate can be known by gas chromatographic analysis and the amount of hydrogen chloride discharged into the gas phase part and can be also easily judged from a temperature change in the reaction system when the quantity of heat removed is already known.

The final supply (total supply) of chlorine is preferably 0.9 mole or more, more preferably 1 mole or more, much more preferably 1.1 moles or more based on 1 mole of the chloropropane represented by the formula (1) initially injected from the viewpoint of reaction efficiency. When the supply of chlorine is excessive, the amount of chlorine which is wasted and does not contribute to the reaction becomes large. Therefore, the total supply of chlorine is preferably 2.5 moles or less, more preferably 2.0 moles or less based on 1 mole of the chloropropane represented by the formula (1) initially injected.

Chlorine may be supplied at a time at the beginning of the reaction or little by little. However, to suppress unpreferred side reactions, it is preferred that chlorine should be supplied little by little over a certain time. The time required for this supply should be set according to the reaction temperature and the size of the reactor, for example, 0.5 to 20 hours, preferably 1 to 10 hours. When it is supplied over a certain time, it may be supplied continuously or intermittently.

More preferably, the feed rate of chlorine should be adjusted to ensure that the amount of the chloropropene intermediate in the reaction system is kept at preferably 30 mass % or less, more preferably 20 mass % or less, much more preferably 10 mass % or less based on the total mass of the reaction system. It is preferred that the feed rate of chlorine should be controlled to ensure that the concentration of chlorine in the reaction system is kept at preferably 10 mass % or less, more preferably 5 mass % or less, much more preferably 3 mass % or less, particularly preferably 1 mass % or less based on the total mass of the reaction system.

The optimal feed rate of chlorine for keeping the concentrations of the chloropropene intermediate and chlorine in the reaction system at the above ranges differs according to the reaction temperature. For example, when the reaction temperature is 0 to 50° C., the feed rate of chlorine is preferably 1 to 2,000 mL/min, more preferably 5 to 1,000 mL/min, much more preferably 10 to 500 mL/min based on 1 mole of the chloropropane represented by the formula (1) initially injected. It is also preferred that the flow rate should be changed within the above range during the progress of the reaction in order to keep the concentration of chlorine in the reaction system at the above range.

Preferably, the feed rate of chlorine is suitably controlled to ensure that the concentrations of the chloropropene intermediate and chlorine in the reaction system fall within the above preferred ranges. That is, when the concentration of the chloropropene in the reaction system is high, when the concentration of chlorine is low, or in the case of both, the supply of chlorine is preferably increased. When the concentration of the chloropropene in the reaction system is low, when the concentration of chlorine is high, or in the case of both, the supply of chlorine is preferably reduced. It is preferred that the supply of chlorine should be controlled while the concentrations of the chloropropene intermediate and chlorine in the reaction system are continuously monitored so that the concentrations of the chloropropene intermediate and chlorine do not deviate from the above preferred ranges. However, even when these concentrations are measured within the reaction time, preferably several times regularly to control the feed rate of chlorine stepwise, the effect of the present invention is not diminished. When the feed rate of chlorine is to be controlled stepwise, it is controlled in preferably 2 to 8 stages, more preferably 3 to 6 stages.

When the supply of chlorine is started while anhydrous aluminum chloride used as a catalyst does not dissolve in the chloropropane represented by the formula (1) at all or dissolves in a very small amount, special attention should be paid to the feed rate of chlorine. In this case, since it takes a certain time to dissolve anhydrous aluminum chloride in the chloropropane represented by the formula (1) completely, the concentration of anhydrous aluminum chloride in the reaction system is low in the initial stage of the reaction and the dehydrochlorination reaction is slow. Therefore, in this case, it is preferred that the feed rate of chlorine should be set low in the initial stage of the reaction and increased from the middle stage of the reaction. Stated more specifically, the supply of chlorine is started at a low rate, for example, 1 to 1,000 mL (STP)/min, preferably 10 to 250 mL/min based on 1 mole of the chloropropane represented by the formula (1) and then the feed rate of chlorine can be set to preferably 1.1 to 10 times, more preferably 1.5 to 5 times the feed rate when the amount of the chloropropane represented by the formula (1) becomes preferably 95% or less, more preferably 90% or less of the amount initially injected. When the supply of chlorine is started after anhydrous aluminum chloride dissolves in the chloropropane represented by the formula (1) sufficiently, it is not necessary to pay attention to this The amount of the chloropropane represented by the formula (1) decreases in the latter stage of the reaction. When the concentration of chlorine is too high in this state, a chlorine substitution reaction of the chloropropene intermediate is promoted and the proportion of a by-product increases. Therefore, in this case, it is preferred to reduce the feed rate of chlorine. Therefore, a method in which the supply of chlorine is reduced when the amount of the chloropropane represented by the formula (1) becomes preferably 30% or less, more preferably 20% or less of the amount initially injected can be advantageously employed. Further, it is preferred to further reduce the feed rate of chlorine when the amount of the chloropropane represented by the formula (1) becomes 10% or less of the amount initially injected. For example, the feed rate can be set to 10 to 90%, preferably 25 to 65% of the feed rate before that time.

Chlorine may be supplied into the gas phase part in the reactor or blown into the reaction solution by inserting an introduction tube into the reaction solution.

The temperature during the supply of chlorine is kept at preferably 0 to 50° C., more preferably 0 to 40° C., much more preferably 10 to 40° C. for the same reason as above. Out of the reactions which occur in the method of the present invention, a chlorine addition reaction is an exothermic reaction, and the whole reaction is an exothermic reaction as well. Therefore, after the supply of chlorine is started, probably, the reaction system needs to be cooled so as to maintain the above temperature range. As the cooling means, any known chemical engineering method can be employed.

Even after the supply of chlorine is stopped, to promote a reaction with dissolved chlorine, the above range is preferably maintained for about 0.1 to 2 hours.

The above description was made by taking mainly a batch type reaction into consideration. The method of the present invention can be carried out as a continuous reaction. In this case, the chloropropane represented by the formula (1) is continuously supplied into the reactor, and the produced chloropropane represented by the formula (2) is continuously extracted. Since anhydrous aluminum chloride is extracted as well at this point, anhydrous aluminum chloride is preferably additionally supplied to keep the amount of anhydrous aluminum chloride in the reaction system at the above range. To supply anhydrous aluminum chloride additionally, a concentrated chloropropane solution of anhydrous aluminum chloride may be prepared separately and added (the chloropropane used may be the chloropropane represented by the formula (1) or the chloropropane represented by the formula (2)), or the chloropropane represented by the formula (1) and solid anhydrous aluminum chloride may be supplied separately. The latter method is preferred because unwanted impurities are not produced.

After the end of the reaction, the produced chloropropane represented by the formula (2) is optionally purified to obtain a product, or when m is 2 in the formula (1) of the chloropropane used as a raw material, the reaction mixture obtained after the first conversion step can be supplied to the second conversion step directly.

The purification step which is preferably carried out to obtain the chloropropane represented by the formula (2) as a product is the same as the step of purifying a chloropropene represented by the formula (3) to be produced by the second conversion step. Therefore, this will be described hereinafter.

Unreacted chlorine in the first conversion step is collected and may be recycled as raw material chlorine for this reaction, or the collected chlorine is purified and may be used as a raw material for another reaction.

A description is subsequently given of the second conversion step.

The second conversion step in the present invention is the step of converting the chloropropane represented by the formula (2) into a chloropropene represented by the formula (3) by raising the temperature of the reaction system by 30° C. or more after the supply of chlorine into the reactor is stopped after the first conversion step as described above.

Also in the second conversion step is catalyzed by anhydrous aluminum chloride which remains in the reaction system as it is. As described above, the chloropropane is dehydrochlorinated by the catalytic action of anhydrous aluminum chloride. The above first reaction is to chlorinate the chloropropene intermediate produced by carrying out this dehydrochlorination reaction in the presence of chlorine right after it is produced. The chloropropane represented by the formula (2) produced by the first conversion step is not dehydrochlorinated at the reaction temperature of the first conversion step even in the presence of anhydrous aluminum chloride. This is because the temperature at which the dehydrochlorination reaction proceeds by anhydrous aluminum chloride differs according to the number of chlorine atoms of the chloropropane as described above.

Therefore, when the temperature of the reaction system is raised to a temperature at which the dehydrochlorination reaction of the chloropropane represented by the formula (2) having one more chlorine atom than the chloropropane represented by the formula (1) as a raw material proceeds after the first conversion step, further after the supply of chlorine is stopped, the chloropropene represented by the formula (3) is obtained.

Since the reaction temperature of the second conversion step differs according to the number of chlorine atoms of the chloropropane like the first conversion step, it will be explained hereinunder, taking as an example a case in which the chloropropane represented by the formula (2) is 1,1,1,2,3-pentachloropropane. As in the case of the first conversion step, when the chloropropane represented by the formula (2) is a compound having a larger number of chlorine atoms than that of 1,1,1,2,3-pentachloropropane, the second conversion step can be carried out in substantially the same manner by suitably setting the reaction temperature higher according to the number of chlorine atoms.

After the end of the first conversion step, the supply of chlorine into the reactor is stopped, after that, preferably, the residual chlorine in the reactor is removed by aeration with an inert gas such as nitrogen, and then the temperature of the reaction system is raised to 30° C. or higher to obtain the chloropropene represented by the formula (3). The reason that the supply of chlorine is stopped before the temperature of the reaction system is raised is that the further addition of chlorine to the produced chloropropene represented by the formula (3) is prevented.

The width of this temperature rise is 30° C. or more, preferably 45° C. or more, particularly preferably 60° C. or more. When the width of the temperature rise is too large and the temperature of the reaction system becomes too high, a side reaction such as the dimerization of the produced chloropropene represented by the formula (3) readily occurs. Therefore, the width of the temperature rise is preferably 150° C. or less, more preferably 140° C. or less.

When the chloropropane represented by the formula (2) is 1,1,1,2,3-pentachloropropane, the temperature of the reaction system after the temperature rise is preferably 80 to 150° C., more preferably 90 to 140° C.

The reaction time is preferably 0.5 to 10 hours.

The chloropropene represented by the formula (3) can be obtained by carrying out the second conversion step in accordance with this method.

After the end of the reaction, the obtained chloropropene represented by the formula (3) is optionally purified to obtain a product.

The chloropropane represented by the formula (2) produced in the first conversion step and the chloropropene represented by the formula (3) produced in the second conversion step can be purified by, for example, distillation.

When the chloropropane represented by the formula (2) is left at a high temperature in the presence of anhydrous aluminum chloride, it is further dehydrochlorinated. Therefore, when the distillation purification of the chloropropane represented by the formula (2) is to be carried out, it is preferably carried out after anhydrous aluminum chloride is removed or deactivated. To remove or deactivate anhydrous aluminum chloride, a method in which a small amount of water is added to the reaction mixture, a method in which anhydrous aluminum chloride is bubbled with a moist gas (such as steam or an inert gas such as nitrogen containing steam), or a method in which anhydrous aluminum chloride is adsorbed to an adsorbent may be employed, and a method in which the reaction mixture after the end of the reaction is left for a long time may also be employed.

The distillation of the chloropropane represented by the formula (2) and the chloropropene represented by the formula (3) is preferably carried out by adding a suitable stabilizer. The stabilizer used herein is the same as the above stabilizer which can be used for the distillation purification of the chloropropane represented by the formula (1).

A distillation apparatus used herein is the same as the above distillation apparatus which can be used for the distillation purification of the chloropropane represented by the formula (1).

Examples

The following examples are provided for the purpose of further illustrating the present invention but are in no way to be taken as limiting.

The apparatus shown in FIG. 1 was used as the reactor unless otherwise stated. An experiment was conducted by blowing a chlorine gas into the reaction solution and discharging a gas comes out to a gas phase while it was unreacted and hydrogen chloride produced by the reaction to the outside of the reactor.

1,1,1,3-tetrachloropropane used as a raw material in the following Examples 1 to 18, Comparative Examples 1 to 3 and Reference Example 1 was obtained by purifying a crude product produced from carbon tetrachloride and ethylene in the presence of an iron-phosphate-based catalyst by distillation. The purity of this 1,1,1,3-tetrachloropropane was 99.5 wt %, and the water content thereof was less than 20 ppm.

Example 1

182 g of purified 1,1,1,3-tetrachloropropane having a purity of 99.5 wt % and 0.10 g of anhydrous aluminum chloride (manufactured by Wako Pure Chemical Industries, Ltd.) were fed to a 200 mL four-necked eggplant flask. The resulting solution was stirred for 1 hour by setting its temperature to 20° C. The solution turned blue after 1 hour, by which it was confirmed that at least part of aluminum chloride was dissolved.

Thereafter, chlorine was supplied at a flow rate of 120 mL/min while the temperature of the solution was kept at 20° C. to start a reaction. After 4 hours, the supply of chlorine was stopped, and chlorine was removed by circulating nitrogen into the reaction solution.

When the reaction solution was analyzed by gas chromatography (GC), the conversion of 1,1,1,3-tetrachloropropane was 100%, and the selectivity of 1,1,1,2,3-pentachloropropane was 92% (yield of 92%).

Examples 2 to 6 and Comparative Examples 1 and 2

A reaction was carried out in the same manner as in Example 1 except that the type and the amount of the catalyst, the reaction temperature (the temperature of the solution set at the time of starting the supply of chlorine) and the reaction time (flow rate of chlorine and time from the start of supplying chlorine to the stoppage of supply) were changed as shown in Table 1.

The results of analysis after the end of the reaction are shown in Table 1.

In Example 2, part of the reaction solution during the reaction, i.e., 8 hours after the start of the reaction was collected and analyzed by GC. As a result, the conversion of 1,1,1,3-tetrachloropropane was 95%, and the selectivity of 1,1,1,2,3-pentachloropropane was 97% (yield of 92%).

In Comparative Examples 1 and 2, anhydrous ferric chloride was used as a catalyst. After 1,1,1,3-tetrachloropropane and the catalyst were fed and stirred for 1 hour at a liquid temperature of 20° C., the resulting solution turned yellow, by which it was confirmed that at least part of the catalyst was dissolved.

Example 7

182 g of 1,1,1,3-tetrachloropropane purified as described above and having a purity of 99.5 wt % and 0.10 g of anhydrous aluminum chloride were fed to a 200 mL four-necked eggplant flask. The temperature of the resulting solution was set to 20° C., and chlorine was supplied at a flow rate of 120 mL/min while the temperature of the solution was kept at 20° C. before the solution turned blue (that is, before anhydrous aluminum chloride was dissolved) to start a reaction. After 5 hours, the supply of chlorine was stopped, and nitrogen was circulated into the reaction solution to remove chlorine.

When the reaction solution was analyzed by gas chromatography (GC), the conversion of 1,1,1,3-tetrachloropropane was 100 and the selectivity of 1,1,1,2,3-pentachloropropane was 84% (yield of 84%).

TABLE 1

Reaction conditions and results

| | Catalyst | | Chlorine | | Reaction | Reaction | Analytical results | | |
|---|---|---|---|---|---|---|---|---|---|
| | Type | Amount (g) | At the start of supply | Flow rate (mL/min) | temperature (° C.) | time (hours) | Conversion (%) | Selectivity (%) | Yield (%) |
| Ex. 1 | AlCl$_3$ | 0.10 | After dissolution of AlCl$_3$ | 120 | 20 | 4 | 100 | 92 | 92 |

TABLE 1-continued

Reaction conditions and results

| | Catalyst | | Chlorine | | Reaction | Reaction | Analytical results | | |
|---|---|---|---|---|---|---|---|---|---|
| | Type | Amount (g) | At the start of supply | Flow rate (mL/min) | temperature (° C.) | time (hours) | Conversion (%) | Selectivity (%) | Yield (%) |
| Ex. 2 | AlCl₃ | 0.10 | After dissolution of AlCl₃ | 60 | 0 | 8 10 | 95 100 | 97 97 | 92 97 |
| Ex. 3 | AlCl₃ | 0.10 | After dissolution of AlCl₃ | 120 | 40 | 4 | 100 | 83 | 83 |
| Ex. 4 | AlCl₃ | 0.50 | After dissolution of AlCl₃ | 60 | 20 | 7 | 100 | 78 | 78 |
| Ex. 5 | AlCl₃ | 1.0 | After dissolution of AlCl₃ | 60 | 20 | 7 | 100 | 75 | 75 |
| Ex. 6 | AlCl₃ | 0.5 | After dissolution of AlCl₃ | 120 | 20 | 4 | 100 | 82 | 82 |
| Ex. 7 | AlCl₃ | 0.10 | Before dissolution of AlCl₃ | 120 | 20 | 5 | 100 | 84 | 84 |
| C. Ex. 1 | FeCl₃ | 0.10 | After dissolution of FeCl₃ | 120 | 20 | 4 | 3 | 22 | 0.7 |
| C. Ex. 2 | FeCl₃ | 0.10 | After dissolution of FeCl₃ | 80 | 65 | 6 | 100 | 65 | 65 |

Ex.: Example
C. Ex.: Comparative Example

Example 8

910 g of purified 1,1,1,3-tetrachloropropane having a purity of 99.5 wt % and 0.18 g of anhydrous aluminum chloride (manufactured by Wako Pure Chemical Industries, Ltd.) were fed to a 1,000 mL four-necked eggplant flask. The resulting solution was stirred for 1 hour by setting its temperature to 20° C. The solution turned blue after 1 hour, by which it was confirmed that at least part of aluminum chloride was dissolved. The concentration of 1,1,3-trichloropropene in the reaction solution at this point was about 1.0 wt %.

Thereafter, a reaction was carried out by changing the flow rate of chlorine in five stages as follows while the temperature of the solution was kept at 20° C.

First, chlorine was supplied at a flow rate of 500 mL/min for 20 minutes. The concentration of each component in the reaction solution after chlorine was supplied was as follows.

1,1,3-trichloropropene: about 3 wt %
1,1,1,3-tetrachloropropane: 90 wt %
Chlorine: 0.17 wt %

Subsequently, chlorine was supplied at a flow rate of 1,000 mL/min for 80 minutes. The concentration of each component in the reaction solution after chlorine was supplied was as follows.

1,1,3-trichloropropene: 0.5 wt %
1,1,1,3-tetrachloropropane: 25 wt %
Chlorine: 0.38 wt %

Thereafter, chlorine was supplied at a flow rate of 500 mL/min for 30 minutes. The concentration of each component in the reaction solution after chlorine was supplied was as follows.

1,1,3-trichloropropene: 0.1 wt % or less
1,1,1,3-tetrachloropropane: 12 wt %
Chlorine: 0.31 wt %

Then, chlorine was supplied at a flow rate of 250 mL/min for 40 minutes. The concentration of each component in the reaction solution after chlorine was supplied was as follows.

1,1,3-trichloropropene: 0.1 wt % or less
1,1,1,3-tetrachloropropane: 5 wt %
Chlorine: 0.58 wt %

Further, chlorine was supplied at a flow rate of 125 mL/min for 40 minutes to terminate the reaction. When the reaction solution was analyzed by GC, the conversion of 1,1,1,3-tetrachloropropane was 99%, and the selectivity of 1,1,1,2,3-pentachloropropane was 96%.

Examples 9 to 11

A reaction was carried out in the same manner as in Example 8 except that the temperature of the solution at the time of adding aluminum chloride and during the reaction (reaction temperature), agitation time after the addition of aluminum chloride and chlorine supply conditions were changed as shown in Table 2. The flow rate of chlorine was changed in 4 stages in Examples 9 and 10 and 5 stages in Example 11.

The results of analysis after the end of the reaction are shown in Table 2.

"TCP concentration" in Table 2 denotes the concentration (wt %) of 1,1,3-trichloropropene in the reaction solution after the addition and agitation of aluminum chloride and before the supply of chlorine.

TABLE 2 reaction conditions and results

| | Reaction conditions | | | | | Analytical results | |
|---|---|---|---|---|---|---|---|
| | Agitation time (minutes) | Reaction temperature (° C.) | TCP concentration (wt %) | Chlorine supply conditions | | Conversion (%) | Selectivity (%) |
| | | | | Order | Conditions | | |
| Ex. 8 | 60 | 20 | approximately 1.0 | 1<br>2<br>3<br>4<br>5 | 500 mL/min. 20 min.<br>1,000 mL/min. 80 min.<br>500 mL/min. 30 min.<br>250 mL/min. 40 min.<br>125 mL/min. 40 min. | 99 | 96 |
| Ex. 9 | 20 | 30 | approximately 0.5 | 1<br>2<br>3<br>4 | 500 mL/min. 20 min.<br>1,000 mL/min. 80 min.<br>500 mL/min. 30 min.<br>250 mL/min. 40 min. | 99 | 93 |
| Ex. 10 | 10 | 40 | approximately 3.7 | 1<br>2<br>3<br>4 | 500 mL/min. 20 min.<br>1,000 mL/min. 100 min.<br>500 mL/min. 20 min.<br>250 mL/min. 20 min. | 100 | 90 |
| Ex. 11 | 5 | 60 | approximately 5 | 1<br>2<br>3<br>4<br>5 | 1,000 mL/min. 10 min.<br>2,500 mL/min. 30 min.<br>1,500 mL/min. 10 min.<br>1,000 mL/min. 40 min.<br>500 mL/min. 20 min. | 100 | 82 |

Ex.: Example

Example 12

The operation of Example 8 was repeated except that anhydrous aluminum chloride in use was changed from the product marketed by Wako Pure Chemical Industries, Ltd. to a product marketed by Nippon Soda Co., Ltd. When the reaction solution was analyzed by GC, the conversion of 1,1,1,3-tetrachloropropane was 100%, and the selectivity of 1,1,1,2,3-pentachloropropane was 96%.

Example 13

720 g of 1,1,1,3-tetrachloropropane purified as described above and having a purity of 99.5 wt % and 0.21 g of anhydrous aluminum chloride (manufactured by Wako Pure Chemical Industries, Ltd.) were fed to a 500 mL four-necked eggplant flask. The resulting solution was stirred for about 1 hour by setting its temperature to 20° C. The solution turned blue, by which it was confirmed that at least part of aluminum chloride was dissolved. At this point, the concentration of 1,1,3-trichloropropene (TCP concentration) in the reaction solution was about 1.1 wt %.

The supply of chlorine was started from this point. Chlorine was first supplied at a flow rate of 400 mL/min for 4 hours and then at 200 mL/min for 30 minutes to carry out a reaction. When the reaction solution after the reaction was analyzed by GC, the conversion of 1,1,1,3-tetrachloropropane was 99%, and the selectivity of 1,1,1,2,3-pentachloropropane was 92%.

Example 14

720 g of 1,1,1,3-tetrachloropropane purified as described above and having a purity of 99.5 wt % and 0.21 g of anhydrous aluminum chloride (manufactured by Wako Pure Chemical Industries, Ltd.) were fed to a 500 mL four-necked eggplant flask. The resulting solution was stirred for about 1 hour by setting its temperature to 20° C. The solution turned blue, by which it was confirmed that at least part of aluminum chloride was dissolved. At this point, the concentration of 1,1,3-trichloropropene in the reaction solution was about 1.2 wt %.

From this point, the reaction solution was stirred for another 30 minutes. The concentration of 1,1,3-trichloropropene in the reaction solution after additional agitation was about 10 wt %.

The supply of chlorine was started from this point. Chlorine was first supplied at a flow rate of 400 mL/min for 6 hours and then at 200 mL/min for 30 minutes to carry out a reaction. When the reaction solution after the reaction was analyzed by GC, the conversion of 1,1,1,3-tetrachloropropane was 99%, and the selectivity of 1,1,1,2,3-pentachloropropane was 90%.

Example 15

A reaction was carried out in the same manner as in Example 14 except that the additional agitation time and the conditions for the 2-stage supply of chlorine (flow rate and time) were changed as shown in Table 3. The GC analytical results of the reaction solution after the reaction are shown in Table 3.

Example 16

Reference Example

A reaction was carried out in the same manner as in Example 14 except that the additional agitation time was changed as shown in Table 3 and the supply of chlorine was carried out in one stage as shown in Table 3. The GC analytical results of the reaction solution after the reaction are shown in Table 3.

TABLE 3 reaction conditions and results

| | TCP concentration before additional agitation (wt %) | Additional agitation | | Chlorine supply conditions | | Conversion (%) | Selectivity (%) |
|---|---|---|---|---|---|---|---|
| | | Time | TCP concentration after additional agitation (wt %) | Flow rate of 400 mL/min in first stage | Flow rate of 200 mL in second stage | | |
| Ex. 13 | 1.1 | 0 | — | 4 hours | 30 min. | 99 | 92 |
| Ex. 14 | 1.2 | 30 min. | 10 | 6 hours | 30 min. | 99 | 90 |
| Ex. 15 | 1.0 | 180 min. | 10 | 8 hours | 30 min. | 99 | 85 |
| Ex. 16 | 1.0 | 24 hours | 77 | 4.5 hours | — | 23 | 0 |

Ex.: Example

When the above Examples 13 to 16 are compared with one another, it is understood that as the time from the start of a dehydrochlorination reaction to the start of supplying chlorine becomes shorter, a reaction after that becomes faster, the reaction time from the start of supplying chlorine becomes shorter, a side reaction is suppressed more, and the selectivity of 1,1,1,2,3-pentachloropropane becomes higher. In addition, when 24 hours elapses after the start of the dehydrochlorination reaction, aluminum chloride rarely serves as a dehydrochlorination catalyst.

Example 17

300 g of 1,1,1,3-tetrachloropropane purified as described above and having a purity of 99.5 wt % was mixed with 200 g of water, and 1,1,1,3-tetrachloropropane was taken out by using a separating funnel. The water content of this 1,1,1,3-tetrachloropropane was 300 ppm.

182 g of this 1,1,1,3-tetrachloropropane containing 300 ppm of water (total water content of 3.0 mmol) and 0.20 g (1.5 mmol) of anhydrous aluminum chloride (manufactured by Wako Pure Chemical Industries, Ltd.) were fed to a 200 mL four-necked eggplant flask. When aluminum chloride is used in this amount, if all water reacts with aluminum chloride to produce aluminum hydroxide, it is calculated that 0.5 mmol of aluminum chloride remains in the reaction solution.

The resulting solution was stirred for 1 hour by setting its temperature to 20° C. The solution turned blue, by which it was confirmed that at least part of aluminum chloride was dissolved.

Thereafter, chlorine was supplied at a flow rate of 120 mL/min for 4 hours while the temperature of the solution was kept at 20° C. After 4 hours, the supply of chlorine was stopped and nitrogen was circulated into the reaction solution to remove chlorine.

When the reaction solution was analyzed by GC after the end of the reaction, the conversion of 1,1,1,3-tetrachloropropane was 100%, and the selectivity of 1,1,1,2,3-pentachloropropane was 93% (yield of 93%).

Comparative Example 3

Reference Example

Like the above Example 17, 182 g of 1,1,1,3-tetrachloropropane having a water content of 300 ppm (total water content of 3.0 mmol) and 0.08 g (0.6 mmol) of anhydrous aluminum chloride (manufactured by Wako Pure Chemical Industries, Ltd.) were fed to a 200 mL four-necked eggplant flask.

When the reaction solution was analyzed by GC after the resulting solution was stirred for 17 hours by setting its temperature to 20° C., the dehydrochlorination reaction of 1,1,1,3-tetrachloropropane into 1,1,3-trichloropropene did not occur and therefore, the conversion of 1,1,1,3-tetrachloropropane was 0%.

The above result is assumed to be because aluminum chloride reacted with water contained in 1,1,1,3-tetrachloropropane to be all converted into aluminum hydroxide and aluminum chloride did not substantially exist in the reaction system.

Reference Example 1

182 g of 1,1,1,3-tetrachloropropane purified as described above and having a purity of 99.5 wt % and 0.10 g of anhydrous aluminum chloride (manufactured by Wako Pure Chemical Industries, Ltd.) were fed to a 200 mL four-necked eggplant flask. The resulting solution was stirred for 1 hour by setting its temperature to 20° C. The solution turned blue, by which it was confirmed that at least part of aluminum chloride was dissolved, and then stirring was further continued for another 5 hours to carry out a reaction.

Thereafter, nitrogen was circulated into the reaction solution to remove hydrogen chloride.

When the conversion of 1,1,1,3-tetrachloropropane was checked by the GC analysis of the reaction solution, it was 13% after 1 hour, 20% after 3 hours and 21% after 5 hours.

Example 18

(1) First Conversion Step 182 g of 1,1,1,3-tetrachloropropane purified as described above and having a purity of 99.5 wt % and 0.06 g of anhydrous aluminum chloride were fed to a 200 mL four-necked eggplant flask, and the resulting solution was stirred for 1 hour by setting its temperature to 20° C. The solution turned blue, by which it was confirmed that at least part of aluminum chloride was dissolved.

Thereafter, the supply of chlorine was started. Chlorine was first supplied at a flow rate of 200 mL/min for 100 minutes, at 100 mL/min for 40 minutes and at 50 mL/min for 20 minutes. Then, the supply of chlorine was stopped, and nitrogen was circulated into the reaction solution to remove chlorine.

When the reaction solution was analyzed by GC, the conversion of 1,1,1,3-tetrachloropropane was 99%, and the selectivity of 1,1,1,2,3-pentachloropropane was 96%.

(2) Second Conversion Step

Thereafter, the above reaction solution was bubbled with nitrogen having a flow rate of 100 mL/min for 12 hours, 0.06 g of anhydrous aluminum chloride was added, and the temperature of the solution was set to 100° C. to carry out a reaction under heating and agitation for 1 hour.

When the reaction solution was analyzed by GC after the end of the reaction, the conversion of 1,1,1,2,3-pentachloropropane was 98%, and the selectivity of 1,1,2,3-tetrachloropropene was 98%.

Example 19

(1) Raw Material Production Step

An SUS autoclave (inner capacity of 1,500 mL) having a stirrer, an ethylene gas introduction port, a gas exhaust port, a port for adding carbon tetrachloride and iron, a port for adding a phosphate and a liquid exhaust port was filled with ethylene. 1,560 g of carbon tetrachloride, 2.0 g of triethyl phosphate and 4.0 g of K100 (coke reduced iron powder of JFE Steel Corporation) were fed to this autoclave, the temperature was set to 110° C., and ethylene was supplied to ensure that the total pressure of a gas phase became 0.5 MPa (abs) so as to carry out an addition reaction between carbon tetrachloride and ethylene. Triethyl phosphate was continuously added at a rate of 0.02 mL/min from the time when the total pressure of the gas phase at 110° C. became 0.5 MPa (abs) to the end of the reaction. The ethylene partial pressure in the gas phase right after the total pressure of the gas phase became 0.5 MPa (abs) was 0.25 MPa.

The addition reaction was carried out while ethylene was continuously supplied to keep the total pressure of the gas phase at 0.5 MPa (abs). It was judged that the reaction was completed when the consumption rate (additional supply rate) of ethylene became 0.1 mol %/min (200 mL/min) based on the initial amount of carbon tetrachloride while it was monitored, and the reaction was terminated.

When the solution after the reaction was extracted and analyzed by GC, the conversion of carbon tetrachloride was 97%, and the selectivity of 1,1,1,3-tetrachloropropane was 96%.

(2) Purification Step after Raw Material Production Step 1,000 g of the reaction solution extracted was fed to a 1-L flask, and batch distillation was carried out by setting the temperature of the solution to 90° C. and the pressure to 10 kPa (abs). A gas reaching the top of the tower was condensed by cooling to collect 910 g of the solution. This collected solution contained about 97 wt % of 1,1,1,3-tetrachloropropane, about 2 wt % of carbon tetrachloride and about 1 wt % of other materials. Triethyl phosphate was not detected in the collected solution.

(3) First Conversion Step 182 g of the above collected solution containing 97 wt % of 1,1,1,3-tetrachloropropane and 0.10 g of anhydrous aluminum chloride (manufactured by Wako Pure Chemical Industries, Ltd.) were fed to a 200 mL four-necked eggplant flask. The resulting solution was stirred for 1 hour by setting its temperature to 20° C. The solution turned blue, by which it was confirmed that at least part of aluminum chloride was dissolved.

The supply of chlorine was started at a flow rate of 120 mL/min to carry out a reaction while the temperature of the solution was kept at 20° C. After 4 hours, the supply of chlorine was stopped, and nitrogen was circulated into the reaction solution to remove chlorine.

When the reaction solution after the end of the reaction was analyzed by GC, the conversion of 1,1,1,3-tetrachloropropane was 100%, and the selectivity of 1,1,1,2,3-pentachloropropane was 94% (the yield of the first conversion step was 94%).

Although the calculated amount of carbon tetrachloride after the raw material production Step and that after the first conversion step did not match completely, this is because carbon tetrachloride could not be condensed and collected completely due to its high vapor pressure. This difference was condensed and collected by an exhaust trap.

Example 20

The raw material production step was carried out in the same manner as in Example 19 to obtain a reaction solution containing 95 wt % of 1,1,1,3-tetrachloropropane. 1,000 g of this reaction solution was fed to a 1-L flask, and batch distillation was carried out by setting the pressure to 10 kPa (abs) to remove materials having a lower boiling point than that of 1,1,1,3-tetrachloropropane and materials having a higher boiling point than that of 1,1,1,3-tetrachloropropane so as to control the purity of 1,1,1,3-tetrachloropropane to 99.9 wt %. Triethyl phosphate was not detected in this 1,1,1,3-tetrachloropropane.

The first conversion step was carried out in the same manner as in the above Example 19 except that 182 g of this 1,1,1,3-tetrachloropropane was used.

When the reaction solution after the end of the reaction was analyzed by GC, the conversion of 1,1,1,3-tetrachloropropane was 100%, and the selectivity of 1,1,1,2,3-pentachloropropane was 93% (the yield of the first conversion step was 93%).

Effect of the Invention

According to the method of the present invention, a reaction for converting a chloropropane represented by the above formula (1) into a chloropropane represented by the above formula (2) can be carried out in a single step. Since this step proceeds at a relatively low reaction temperature, energy required for the reaction is small. In addition, the yield of the chloropropane of interest is high.

According to the method of the present invention, further, a reaction for converting the chloropropane represented by the above formula (2) into a chloropropene represented by the above formula (3) can be carried out substantially without producing liquid waste to be disposed of. In addition, the reaction conversion and the selectivity of a product of interest are high.

Therefore, the method of the present invention is extremely useful industrially.

The invention claimed is:

1. A method of producing a chlorinated hydrocarbon having 3 carbon atoms, comprising a conversion step for converting a chloropropane represented by the following formula (1) into a chloropropane represented by the following formula (2) by reacting said chloropropane represented by the formula (1) with chlorine in the presence of anhydrous aluminum chloride at a temperature from 0° C. to 40° C., $$CCl_3-CCl_{(2-m)}H_m-CCl_{(3-n)}H_n \qquad (1),$$

wherein, in the above formula (1), m is 1 or 2, and n is an integer of 0 to 3,

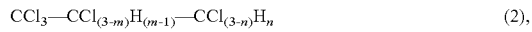

wherein, in the above formula (2), m and n are the same integers as in the formula (1), respectively.

2. The method of producing a chlorinated hydrocarbon having 3 carbon atoms according to claim 1, wherein the conversion step is carried out by putting at least the chloropropane represented by the above formula (1) and anhydrous aluminum chloride into a reactor and then supplying chlorine into the reactor.

3. The method of producing a chlorinated hydrocarbon having 3 carbon atoms according to claim 2, wherein the supply of chlorine into the reactor is started after anhydrous aluminum chloride is dissolved.

4. The method of producing a chlorinated hydrocarbon having 3 carbon atoms according to claim 1, wherein the conversion step is carried out by putting a solution containing at least anhydrous aluminum chloride and the chloropropane represented by the above formula (1) into a reactor and then supplying chlorine into the reactor.

5. The method of producing a chlorinated hydrocarbon having 3 carbon atoms according to claim 4, wherein the solution containing at least anhydrous aluminum chloride and the chloropropane represented by the above formula (1) is obtained by putting a solution prepared outside the reactor by dissolving anhydrous aluminum chloride in a solvent into the reactor and then diluting the solution with the chloropropane represented by the above formula (1).

6. The method of producing a chlorinated hydrocarbon having 3 carbon atoms according to claim 5, wherein the solvent used in the solution prepared outside the reactor is the chloropropane represented by the above formula (1).

7. The method of producing a chlorinated hydrocarbon having 3 carbon atoms according to claim 1, wherein the anhydrous aluminum chloride is obtained by putting the chloropropane represented by the above formula (1) and metal aluminum into a reactor and supplying at least one selected from the group consisting of chlorine and hydrogen chloride into the reactor to convert the metal aluminum into aluminum chloride.

8. The method of producing a chlorinated hydrocarbon having 3 carbon atoms according to claim 1, wherein m in the above formula (1) is 2, and the method further comprises a second conversion step for converting the chloropropane represented by the above formula (2) into a chloropropene represented by the following formula (3) by raising the temperature of the reaction system by 30° C. or more after the supply of chlorine into the reactor is stopped after the second conversion step,

wherein, in the above formula (3), n is the same integer as in the formula (1).

9. The method of producing a chlorinated hydrocarbon having 3 carbon atoms according to claim 1, wherein n in the above formula (1) is an integer of 0 to 2, and the compound represented by the above formula (1) is obtained through a step for adding carbon tetrachloride to an unsaturated hydrocarbon having 2 carbon atoms represented by the following formula (0) in the presence of an iron-phosphate catalyst and a step for removing the phosphate from the addition product obtained in the addition step,

wherein, in the above formula (0), m and n are the same integers as in the formula (1), respectively, but n cannot be 3.

10. The method of producing a chlorinated hydrocarbon having 3 carbon atoms according to claim 2, wherein m in the above formula (1) is 2, and the method further comprises a second conversion step for converting the chloropropane represented by the above formula (2) into a chloropropene represented by the following formula (3) by raising the temperature of the reaction system by 30° C. or more after the supply of chlorine into the reactor is stopped after the second conversion step,

wherein, in the above formula (3), n is the same integer as in the formula (1).

11. The method of producing a chlorinated hydrocarbon having 3 carbon atoms according to claim 3, wherein m in the above formula (1) is 2, and the method further comprises a second conversion step for converting the chloropropane represented by the above formula (2) into a chloropropene represented by the following formula (3) by raising the temperature of the reaction system by 30° C. or more after the supply of chlorine into the reactor is stopped after the second conversion step,

wherein, in the above formula (3), n is the same integer as in the formula (1).

12. The method of producing a chlorinated hydrocarbon having 3 carbon atoms according to claim 4, wherein m in the above formula (1) is 2, and the method further comprises a second conversion step for converting the chloropropane represented by the above formula (2) into a chloropropene represented by the following formula (3) by raising the temperature of the reaction system by 30° C. or more after the supply of chlorine into the reactor is stopped after the second conversion step,

wherein, in the above formula (3), n is the same integer as in the formula (1).

13. The method of producing a chlorinated hydrocarbon having 3 carbon atoms according to claim 5, wherein m in the above formula (1) is 2, and the method further comprises a second conversion step for converting the chloropropane represented by the above formula (2) into a chloropropene represented by the following formula (3) by raising the temperature of the reaction system by 30° C. or more after the supply of chlorine into the reactor is stopped after the second conversion step,

wherein, in the above formula (3), n is the same integer as in the formula (1).

14. The method of producing a chlorinated hydrocarbon having 3 carbon atoms according to claim 6, wherein m in the above formula (1) is 2, and the method further comprises a second conversion step for converting the chloropropane represented by the above formula (2) into a chloropropene represented by the following formula (3) by raising the temperature of the reaction system by 30° C. or more after the supply of chlorine into the reactor is stopped after the second conversion step,

wherein, in the above formula (3), n is the same integer as in the formula (1).

15. The method of producing a chlorinated hydrocarbon having 3 carbon atoms according to claim 7, wherein m in the above formula (1) is 2, and the method further comprises a second conversion step for converting the chloropropane represented by the above formula (2) into a chloropropene represented by the following formula (3) by raising the temperature of the reaction system by 30° C. or more after the supply of chlorine into the reactor is stopped after the second conversion step, $$CCl_2=CCl-CCl_{(3-n)}H_n \qquad (3),$$

wherein, in the above formula (3), n is the same integer as in the formula (1).

16. The method of producing a chlorinated hydrocarbon having 3 carbon atoms according to claim 2, wherein n in the above formula (1) is an integer of 0 to 2, and the compound represented by the above formula (1) is obtained through a step for adding carbon tetrachloride to an unsaturated hydrocarbon having 2 carbon atoms represented by the following formula (0) in the presence of an iron-phosphate catalyst and a step for removing the phosphate from the addition product obtained in the addition step, $$CCl_{(2-m)}H_m=CCl_{(2-n)}H_n \qquad (0),$$

wherein, in the above formula (0), m and n are the same integers as in the formula (1), respectively, but n cannot be 3.

17. The method of producing a chlorinated hydrocarbon having 3 carbon atoms according to claim 3, wherein n in the above formula (1) is an integer of 0 to 2, and the compound represented by the above formula (1) is obtained through a step for adding carbon tetrachloride to an unsaturated hydrocarbon having 2 carbon atoms represented by the following formula (0) in the presence of an iron-phosphate catalyst and a step for removing the phosphate from the addition product obtained in the addition step, $$CCl_{(2-m)}H_m=CCl_{(2-n)}H_n \qquad (0),$$

wherein, in the above formula (0), m and n are the same integers as in the formula (1), respectively, but n cannot be 3.

18. The method of producing a chlorinated hydrocarbon having 3 carbon atoms according to claim 4, wherein n in the above formula (1) is an integer of 0 to 2, and the compound represented by the above formula (1) is obtained through a step for adding carbon tetrachloride to an unsaturated hydrocarbon having 2 carbon atoms represented by the following formula (0) in the presence of an iron-phosphate catalyst and a step for removing the phosphate from the addition product obtained in the addition step, $$CCl_{(2-m)}H_m=CCl_{(2-n)}H_n \qquad (0),$$

wherein, in the above formula (0), m and n are the same integers as in the formula (1), respectively, but n cannot be 3.

19. The method of producing a chlorinated hydrocarbon having 3 carbon atoms according to claim 5, wherein n in the above formula (1) is an integer of 0 to 2, and the compound represented by the above formula (1) is obtained through a step for adding carbon tetrachloride to an unsaturated hydrocarbon having 2 carbon atoms represented by the following formula (0) in the presence of an iron-phosphate catalyst and a step for removing the phosphate from the addition product obtained in the addition step, $$CCl_{(2-m)}H_m=CCl_{(2-n)}H_n \qquad (0),$$

wherein, in the above formula (0), m and n are the same integers as in the formula (1), respectively, but n cannot be 3.

20. The method of producing a chlorinated hydrocarbon having 3 carbon atoms according to claim 6, wherein n in the above formula (1) is an integer of 0 to 2, and the compound represented by the above formula (1) is obtained through a step for adding carbon tetrachloride to an unsaturated hydrocarbon having 2 carbon atoms represented by the following formula (0) in the presence of an iron-phosphate catalyst and a step for removing the phosphate from the addition product obtained in the addition step, $$CCl_{(2-m)}H_m=CCl_{(2-n)}H_n \qquad (0),$$

wherein, in the above formula (0), m and n are the same integers as in the formula (1), respectively, but n cannot be 3.

21. The method of producing a chlorinated hydrocarbon having 3 carbon atoms according to claim 1, wherein the reaction system is cooled during the supply of chlorine so that the temperature in the reaction system is kept at 10° C. to 40° C.

* * * * *